(12) United States Patent
Mendes et al.

(10) Patent No.: US 10,087,177 B2
(45) Date of Patent: Oct. 2, 2018

(54) PROCESS FOR THE PREPARATION OF ACLIDINIUM BROMIDE

(71) Applicant: Hovione Scientia Limited, Cork (IE)

(72) Inventors: Zita Mendes, Lisbon (PT); Constança Cacela, Lisbon (PT); Ana Carina Constantino, Charneca da Caparica (PT); Bruno Santos, Odivelas (PT)

(73) Assignee: Hovione Scientia Limited, Cork (IE)

( * ) Notice: Subject to any disclaimer, the term of this patent is extended or adjusted under 35 U.S.C. 154(b) by 0 days.

(21) Appl. No.: 15/562,814

(22) PCT Filed: Mar. 30, 2016

(86) PCT No.: PCT/GB2016/050888
§ 371 (c)(1),
(2) Date: Sep. 28, 2017

(87) PCT Pub. No.: WO2016/156836
PCT Pub. Date: Oct. 6, 2016

(65) Prior Publication Data
US 2018/0105517 A1    Apr. 19, 2018

(30) Foreign Application Priority Data
Mar. 30, 2015  (PT) .......................................... 108370

(51) Int. Cl.
| | | |
|---|---|---|
| *C07D 453/02* | (2006.01) | |
| *A61P 11/08* | (2006.01) | |
| *A61K 9/00* | (2006.01) | |
| *A61K 31/439* | (2006.01) | |
| *A61K 47/26* | (2006.01) | |
| *B01D 9/00* | (2006.01) | |

(52) U.S. Cl.
CPC .......... *C07D 453/02* (2013.01); *A61K 9/0075* (2013.01); *A61K 31/439* (2013.01); *A61K 47/26* (2013.01); *A61P 11/08* (2018.01); *B01D 9/005* (2013.01); *B01D 9/0027* (2013.01); *C07B 2200/13* (2013.01)

(58) Field of Classification Search
CPC .................................................. C07D 453/02
See application file for complete search history.

(56) References Cited

FOREIGN PATENT DOCUMENTS

| | | |
|---|---|---|
| PT | 108370 | 3/2015 |
| WO | 0104118 A2 | 1/2001 |
| WO | 2005014044 A1 | 2/2005 |
| WO | 2008009397 A1 | 1/2008 |
| WO | 2014027045 A1 | 2/2014 |
| WO | 2015062560 A1 | 5/2015 |
| WO | 2015071824 A1 | 5/2015 |
| WO | 2016156836 A1 | 10/2016 |

OTHER PUBLICATIONS

Foreign Communication from a related application—International Search Report and Written Opinion of International Application No. PCT/GB2016/050888 dated Jul. 5, 2016, 13 pages.
Foreign Communication from a related application—International Preliminary Report on Patentability of International Application No. PCT/GB2016/050888 dated Jun. 16, 2017, 22 pages.
Prat, Maria, et al., "Discovery of Novel Quaternary Ammonium Derivatives of (3R)-Quinuclidinol Esters as Potent and Long-Acting Muscarinic Antagonists with Potential for Minimal Systemic Exposure after Inhaled Administration: Identification of (3R)-3-([Hydroxy(di-2-thienyl)acetyl]oxy}-1-(3-phenoxypropyl)-1-azoniabicyclo[2.2.2]octane Bromide (Aclidinium Bromide)," J. Med. Chem., 2009, pp. 5076-5092, vol. 52, No. 16, American Chemical Society, XP055024812.

*Primary Examiner* — Joseph R Kosack
*Assistant Examiner* — Karen Cheng
(74) *Attorney, Agent, or Firm* — Conley Rose, P.C.; Rodney B. Carroll (57) ABSTRACT

A process for preparing (3R)-3-[2-Hydroxy(di-2-thienyl) acetoxy]-1-(3-phenoxypropyl)-1-azoniabicyclo[2.2.2]octane bromide (aclidinium bromide) comprises reacting 2-hydroxy-2,2-dithien-2-ylacetic acid 1-azabicyclo[2.2.2]oct-3 (R) yl methyl ester and 3-phenoxypropyl bromide, wherein the reaction takes place in a solvent or mixture of solvents selected from the group of amides and/or the group of solvents with a sulfoxide group. Also provided is a crystalline aclidinium bromide characterized by a powder XRPD pattern having peaks at 7.7±0.2° 2θ, 10.4±0.2° 2θ, 13.2±0.2° 2θ, 13.8±0.2° 2θ, 19.9±0.2° 2θ, 20.3±0.2° 2θ, 20.8±0.2° 2θ, 24.2±0.2° 2θ, 25.7±0.2° 2θ, 26.1±0.2° 2θ, 29.2±0.2° 2θ, 30.8±0.2° 2θ. A pharmaceutical composition comprises aclidinium bromide according to the invention and a pharmaceutically acceptable excipient.

35 Claims, 5 Drawing Sheets

PROCESS FOR THE PREPARATION OF ACLIDINIUM BROMIDE

CROSS REFERENCE TO RELATED APPLICATIONS

This application is a filing under 35 U.S.C. 371 of International Application No. PCT/GB2016/050888 filed Mar. 30, 2016, entitled "Process for the Preparation of Aclidinium Bromide" which claims priority to Portuguese Patent Application No. 108370 filed Mar. 30, 2015, which applications are incorporated by reference herein in their entirety.

FIELD OF INVENTION

The present invention relates to a process for the preparation of aclidinium salts, particularly aclidinium bromide. The invention also concerns a pharmaceutical composition comprising aclidinium in the form of a dry powder, solution or suspension.

BACKGROUND OF THE INVENTION

The present invention relates to a novel process for the preparation of aclidinium salts. The chemical name of aclidinium is (3R)-3-[2-hydroxy(di-2-thienyl)acetoxy]-1-(3-phenoxypropyl)-1-azoniabicyclo[2.2.2]octane. The structure of the aclidinium salts is depicted below (I).

wherein:
X⁻ is a pharmaceutically acceptable anion, such as bromide, chloride or iodide.

The preferred salt is aclidinium bromide, a quaternary ammonium salt.

Aclidinium bromide is a white to off-white crystalline powder. The active form is the R-isomer and the S-isomer has small affinity for muscarinic receptors in vitro and limited effect on acetylcholine induced bronchoconstriction. The drug is formulated as an inhalation powder, comprised of a mixture of micronized aclidinium bromide and α-lactose monohydrate.

Aclidinium bromide is a muscarinic antagonist and is available commercially as Bretaris Genuair (EU Members States), Tudorza Pressair (US and Canada) and Eklira Genuair (UK).

This compound as well as a process for its manufacture is described in WO 01/04118. Later, an improved process was described in WO2008/009397 and also presented in the article J. Med. Chem. 2009, 52, 5076-5092.

The process of aclidinium bromide described in WO 01/04118 has two main disadvantages:
  The use of a potential genotoxic reagent—3-phenoxypropyl bromide with a large excess—5 equivalents
  A long reaction time—72 hours.

The process described in WO2008/009397 aims at overcoming these disadvantages by using specific groups of solvents, reducing the amount of 3-phenoxypropyl bromide and controlling the content of this reagent in the final product.

This process is able to reduce the reaction time to 8 hours, using a specific solvent (ketones or cyclic ethers having a boiling point between 50° C. and 210° C.) while using a reduced amount of the reagent 3-phenoxypropyl bromide. However this comes at the cost of performing the reaction under reflux.

Moreover, taking into account that the solvents considered have boiling points from 50° C. and 210° C., the reaction temperature, in some cases, must be extremely high, which brings extra operational challenges to the process.

SUMMARY OF INVENTION

We have now devised a process which consistently affords product with high chemical purity, higher than 99.0% preferably over 99.5%, and a consistent polymorphic form, whilst minimizing or eliminating the disadvantages referred to above. The present process also enables the manufacture of a product with controlled particle size.

According to one aspect of the present invention, there is provided a process for preparing (3R)-3-[2-Hydroxy(di-2-thienyl)acetoxy]-1-(3-phenoxypropyl)-1-azoniabicyclo[2.2.2]octane bromide (aclidinium bromide) by reacting 2-hydroxy-2,2-dithien-2-ylacetic acid 1-azabicyclo[2.2.2]oct-3(R) yl methyl ester and 3-phenoxypropyl bromide, wherein the reaction takes place in a solvent or mixture of solvents that are selected from the group of amides and/or the group of solvents with a sulfoxide group.

In another aspect, the present invention provides a crystalline aclidinium bromide characterized by a powder XRPD pattern having peaks at 7.7±0.2° 2θ, 10.4±0.2° 2θ, 13.2±0.2° 2θ, 13.8±0.2° 2θ, 19.9±0.2° 2θ, 20.3±0.2° 2θ, 20.8±0.2° 2θ, 24.2±0.2° 2θ, 25.7±0.2° 2θ, 26.1±0.2° 2θ, 29.2±0.2° 2θ, 30.8±0.2° 2θ.

Figure 9:
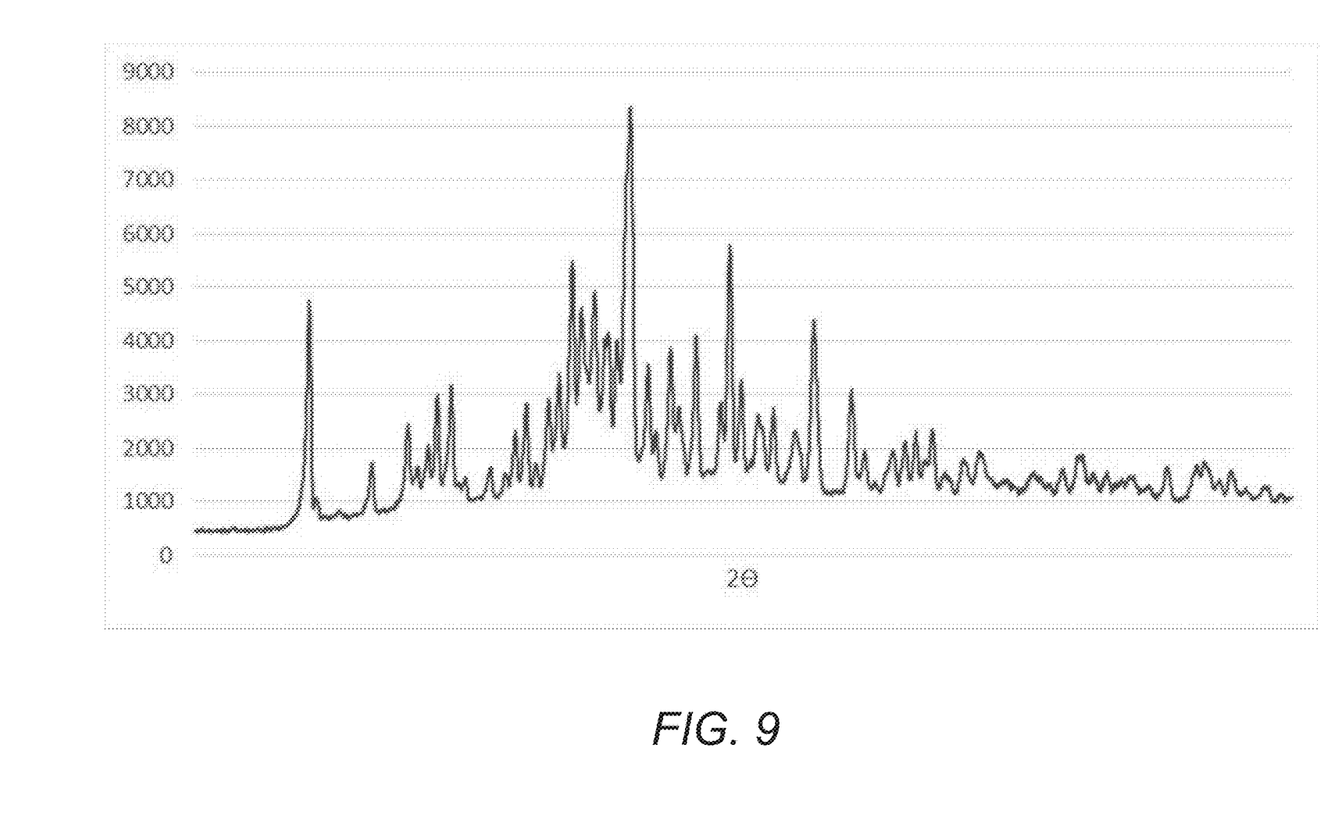
FIG. 9—depicts a powder XRPD pattern of a mixture of crystalline and amorphous aclidinium bromide.

In another aspect, the present invention provides a mixture of crystalline and amorphous aclidinium bromide, optionally obtainable according to the process described herein, characterized by a powder XRPD pattern as depicted in FIG. 9:

In another aspect, the present invention provides a process of preparing aclidinium bromide, which process comprises drying a solution of aclidinium bromide in a solvent or a mixture of solvents, preferably by spray drying.

In another aspect, the present invention provides a pharmaceutical composition comprising a pharmaceutically acceptable salt of aclidinium, preferably aclidinium bromide, as disclosed herein and a pharmaceutically acceptable excipient. Preferably, the aclidinium bromide is made according to the process described herein.

In another aspect, the present invention provides aclidinium bromide as disclosed herein, or aclidinium bromide obtained according to the process as disclosed herein; or a pharmaceutical composition comprising aclidinium bromide as disclosed herein for use in medicine, preferably for use in treating chronic obstructive pulmonary disease (COPD).

The preparation of aclidinium bromide involves a transesterification reaction between 3R-quinucidinol (II) and MDTG (III) to produce N-despropylaclidinium (IV), followed by the reaction of N-despropylaclidinium with 3-phenoxypropyl bromide (V) (quaternization reaction) to synthesize aclidinium bromide (Scheme 1).

For the transesterification reaction a variety of bases can be used, among others: K₂CO₃, sodium methoxide, sodium ethoxide, sodium tert butoxide, triazabicyclodecene (TBD) and 1,8-Diazabicyclo[5.4.0]undec-7-ene (DBU).

By using a different solvent or a mixture of solvents in the quaternization reaction, the process of the present invention is able to overcome the disadvantages of the prior art while carrying out the reaction at a temperature below 100° C., namely at temperatures around room temperature, most preferably at temperatures from 20 to 30° C., preferably at a temperature around 30° C. or 20° C.

Surprisingly, the reaction time is maintained at less than 8 hours, preferably less than 6 hours, more preferably less than 4 hours, and the amount of genotoxic reagent used is preferably maintained in the range of 1.2 to 2.0 mole equivalents.

The solvent chosen can be a solvent with a sulfoxide group, preferably dimethylsulfoxide (DMSO), diethylsulfoxide, or any of the solvents of the amide group, preferably dimethylformamide (DMF), (dimethylacetamide) DMA, or mixtures thereof.

A further advantage of the quaternization reaction described is that the solid material thus obtained can be micronized to achieve the desired particle size range, for example a particle size distribution suitable for inhalation.

DETAILED DESCRIPTION OF THE INVENTION

This invention concerns a process for preparing (3R)-3-[2-Hydroxy(di-2-thienyl)acetoxy]-1-(3-phenoxypropyl)-1-azoniabicyclo[2.2.2]octane bromide by reacting (3R)-1-azabicyclo[2.2.2]oct-3-yl hydroxy(di-2-thienyl)acetate and 3-phenoxypropyl bromide, wherein the reaction takes place in a solvent or mixture of solvents that are selected from the group of amides and/or other solvents or mixture of solvents with a sulfoxide group at a temperature below their boiling point. The reaction temperature is below 100° C., preferably below 50° C., and in preferred aspects the reaction temperature is from about 30° C. to about 20° C., suitably about 30° C., or about 20° C.

In a preferred aspect, the reaction takes place under a flow of an inert gas, suitably a dry inert gas, preferably under a flow of dry nitrogen, dry helium or a mixture thereof.

In a preferred aspect, the reaction takes place at a pressure below the atmospheric pressure. Standard atmospheric pressure is 101325 Pa (equivalent to 760 mmHg), and preferably the pressure is below this. Alternatively, the pressure may be below the ambient atmospheric pressure, based on the location where the reaction is taking place.

Preferably, any alcohol formed during the reaction is removed from the reaction mixture.

Preferably, the reaction solvent is DMF or is a mixture of solvents containing DMF, DMA or a mixture of solvents containing DMA, DMSO or a mixture of solvents containing DMSO. One preferred solvent is DMSO or a mixture of solvents containing DMSO.

For example, when using DMSO as solvent the purity achieved is above 99.5% without the need for any crystallization step. For other solvents a crystallization step may be needed in order to achieve the desired purity.

In a preferred aspect, the process of the invention is such that the equivalent mole ratio of 3-phenoxypropyl bromide to (3R)-1-azabicyclo[2.2.2]oct-3-yl hydroxy(di-2-thienyl) acetate is in the range of from 1.2 to 2.0, preferably from 1.5 to 2.0, more preferably about 1.8.

The content of the genotoxic impurity 3-phenoxypropyl bromide in the final product is always below 500 ppm, more preferably below 200 ppm.

The process of the invention preferably has a total reaction time is not more than 8 hours. In a preferred aspect, the reaction time is not more than 6 hours, more preferably not more than 4 hours.

The process of the invention may if desired further comprise the step of purification of aclinidium bromide by dissolving the product in DMSO (or another suitable solvent) and using acetonitrile (or another suitable solvent) as co-solvent to precipitate the purified product.

In a preferred process according to the invention, the aclidinium bromide obtained is crystalline.

In one preferred aspect of the process according to the invention, the aclidinium bromide obtained is a mixture of crystalline and amorphous material.

Figure 1:
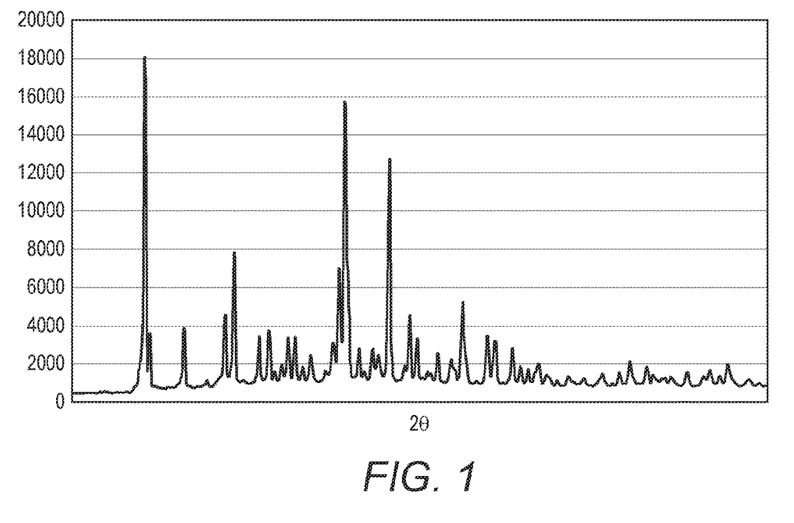
FIG. 1—depicts the powder XRPD pattern of an anhydrous crystalline form of aclidinium bromide.

In a preferred aspect of the invention, an anhydrous crystalline form of aclidinium bromide is obtained. This form is characterized by the powder XRPD pattern depicted in the FIG. 1 and having characteristic diffraction peaks at 7.7±0.2° 2θ, 10.4±0.2° 2θ, 13.2±0.2° 2θ, 13.8±0.2° 2θ, 19.9±0.2° 2θ, 20.3±0.2° 2θ, 20.8±0.2° 2θ, 24.2±0.2° 2θ, 25.7±0.2° 2θ, 26.1±0.2° 2θ, 29.2±0.2° 2θ, 30.8±0.2° 2θ.

This anhydrous crystalline form can be obtained with different crystal habits and morphologies.

This crystalline form of aclidinium bromide is preferably further characterized by no weight loss by TGA, and also preferably further characterized by a DSC thermogram having an endotherm peak at 228° C.

In one aspect, the crystalline form of aclidinium bromide provided may comprise a minor amount of amorphous aclidinium bromide. Suitably, the amount is less than 20% by weight, preferably less than 10% by weight, more preferably less than 5% by weight (% by weight being expressed with respect to the total amount of material).

Figure 2:
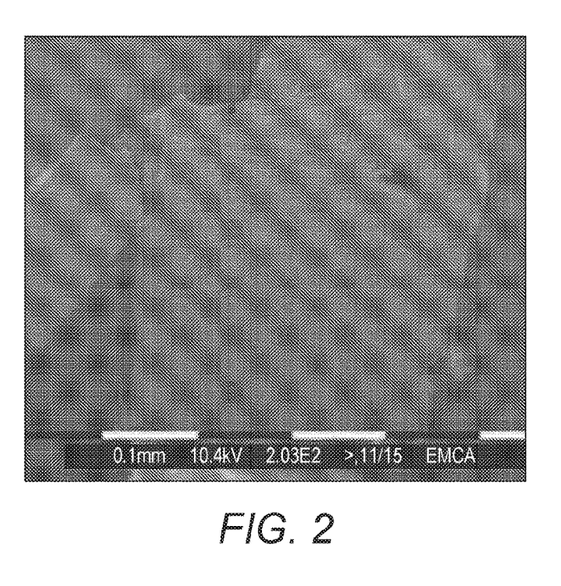
FIG. 2—depicts the Scanning Electron Microscopy (SEM) of the product with particles presenting plate like shape particles.

Different morphology was observed when anti-solvent crystallization technique was conducted. The particles exhibited a plate like shape by Electro Scanning Microscopy (SEM) analysis as shown in FIG. 2.

Figure 3:
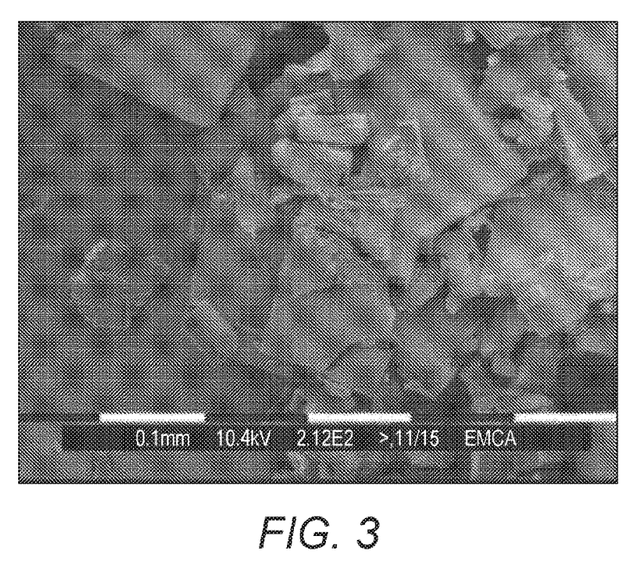
FIG. 3—depicts the Scanning Electron Microscopy (SEM) of the product with particles presenting cube-shape particles.

When a thermocycling process is used to crystallize the product, cube-shape particles are obtained, as shown in FIG. 3.

Figure 4:
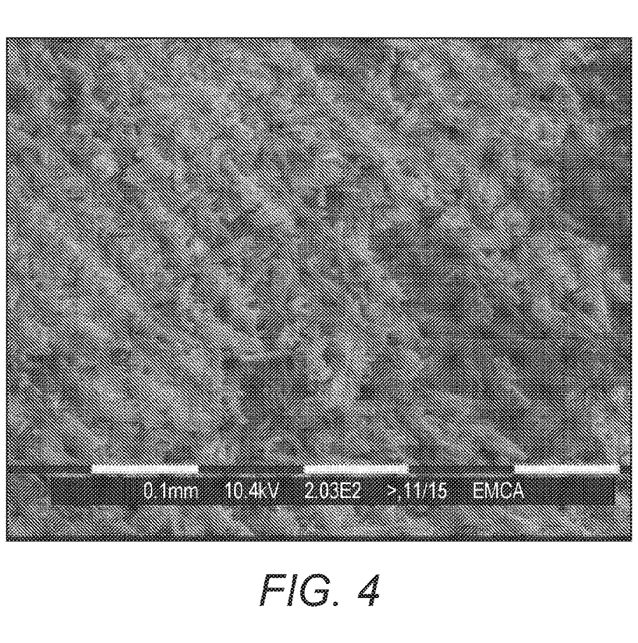
FIG. 4—depicts the Scanning Electron Microscopy (SEM) of the product with particles presenting very small parallel piped shape particles.

And when crystallization is carried out by cooling the reaction mixture, the product morphology consists of very small parallel piped shape particles, as shown in FIG. 4.

Figure 5:
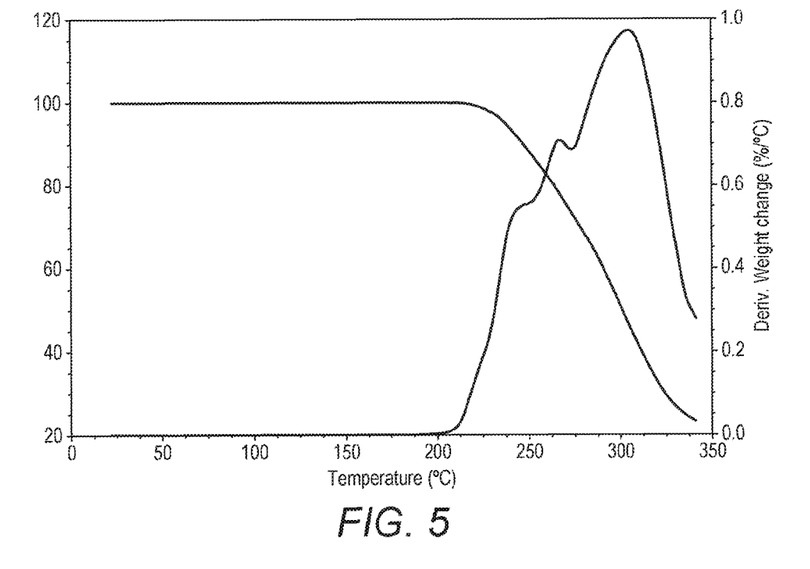
FIG. 5—depicts the Thermal Gravimetric Analysis of anhydrous aclidinium bromide.

Anhydrous crystalline aclidinium bromide obtained according to the process described herein is further characterized by no weight loss until melting and decomposition by Thermal Gravimetric Analysis (TGA) FIG. 5.

Figure 6:
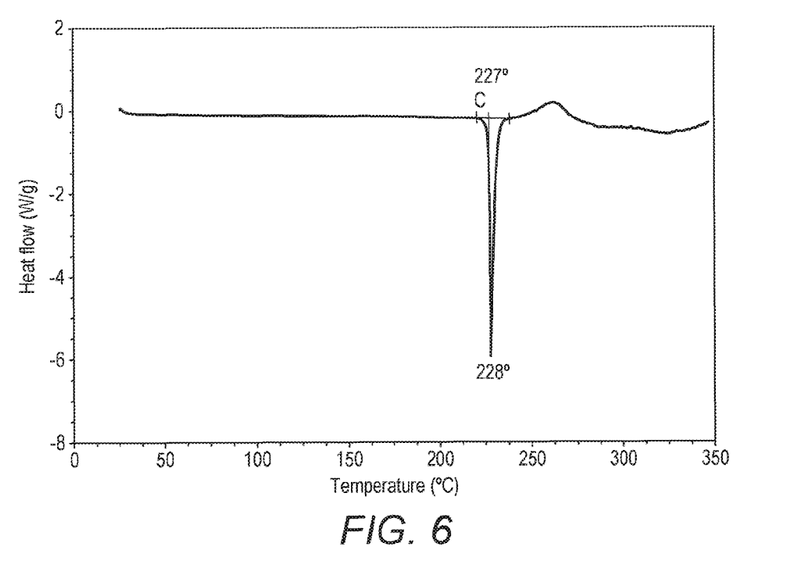
FIG. 6—depicts a Differential Scanning calorimetry (DSC) of anhydrous aclidinium bromide.

Anhydrous crystalline aclidinium bromide is further characterized by a Differential Scanning calorimetry (DSC) thermogram—FIG. 6—having a single endothermic transition, at a temperature given by the onset of the transition (Tonset) of 227° C. This transition corresponds to the melting of the crystalline form.

The invention also concerns a process to obtain aclidinium salts, preferably aclidinium bromide, by drying a solution of the aclidinium salt in a solvent or in a mixture of solvents by lyophilization or spray drying or by another suitable drying method. Preferably the drying step is a spray drying step.

In one preferred aspect, said solvent or a mixture of solvents are selected from solvents with a sulfoxide group. Preferably the said mixture contains DMSO and most preferably the solvent is DMSO.

In a preferred aspect, when the drying step is a spray drying process, the product obtained can either be crystalline, crystalline with a minor content of amorphous product, pure amorphous, amorphous with a minor content of a crystalline form or a mixture of amorphous and crystalline forms in different ratios.

Figure 7:
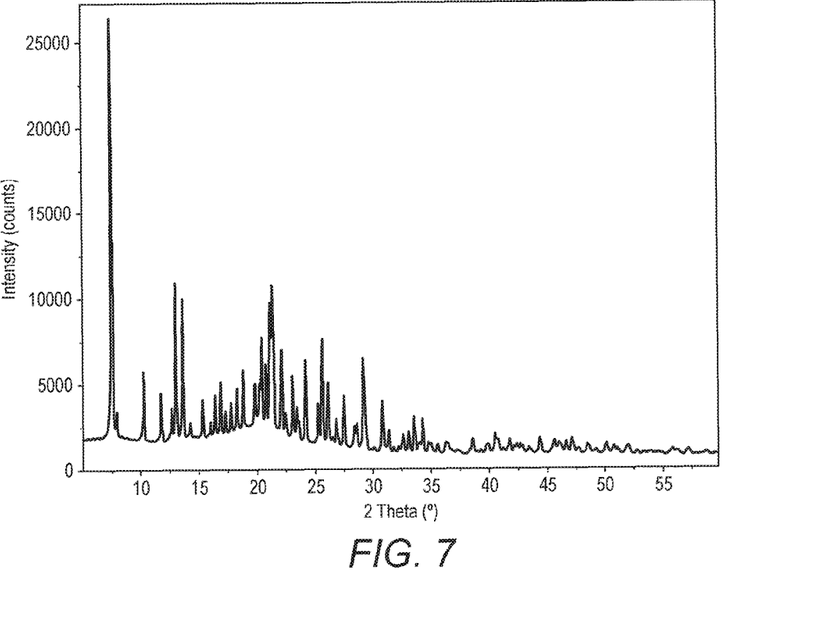
FIG. 7—depicts a XRPD pattern of a mixture of crystalline form and amorphous aclidinium bromide obtained by spray drying process.

The XRPD pattern (FIG. 7) depicts a mixture of a crystalline form and amorphous aclidinium bromide obtained by a spray drying process.

The invention also concerns a pharmaceutical composition comprising aclidinium, preferably in the form of a dry powder, solution or suspension of a pharmaceutical acceptable salt, which can for example be anhydrous, a hydrate or a solvate as described above in admixture with a pharmaceutical excipient, preferably an acceptable dry powder carrier.

Preferably, the pharmaceutical acceptable salt form is aclidinium bromide.

Suitably, the pharmaceutical acceptable carrier is lactose or α-lactose monohydrate.

The invention also provides a pharmaceutical composition as described herein for inhalation comprising aclidinium in the form of a dry powder, solution or suspension of a pharmaceutically acceptable salt as described in herein or as obtained by a process as described herein, together with a pharmaceutically acceptable excipient.

Preferably, the pharmaceutical composition is in the form of a dry powder formulation where the pharmaceutically acceptable excipient is an acceptable dry powder carrier. The pharmaceutically acceptable carrier is preferably lactose or α-lactose monohydrate.

The invention can encompass a pharmaceutical composition as described herein wherein aclidinium bromide is replaced with an alternative pharmaceutically acceptable salt form of aclidinium. However, the salt form used is preferably aclidinium bromide.

For example, the chloride or the iodide salts may be used. The synthetic route for these salts is essentially identical to the process for making the bromide salt, except that a suitable chloride or iodide reagent should be used. For example, 3-phenoxypropyl chloride may be used instead of 3-phenoxypropyl bromide.

EXAMPLES

This invention is illustrated by the following examples. These examples are provided to illustrate particular aspects of the disclosure and do not limit the scope of the present invention.

HPLC analysis of the products of the following examples was conducted on a Zorbaz SB-C3 column (150 mm×3.0 mm×3.5 µm).

The mobile phase at a flow of 1.2 ml/min was a binary system of water (containing sodium methanesulfonate and potassium dihydrogenphosphate at pH3.0—Phase A) and a mixture of methanol:acetonitrile:phase A (10:40:50 v/v/v). The total run time was 50 minutes.

Example 1—Transesterification Reaction

Synthesis of (3R)-azabicyclo[2.2.2]oct-3-yl hydroxy (di-2-thienyl)acetate (Compound IV)

To a solution of (3R)-quinuclidinol (10.30 g, 81.0 mmol) in 500 ml of toluene was added methyl di(2-thienyl)glycolate (MDTG) (20 g, 78 mmol). The solution was refluxed with continuous distillation of toluene and replacement with fresh toluene.

After distillation was added sodium methoxide (1.70 g, 31 mmol) and distillation was carried out at 80°/90° C. under a flow of nitrogen, until the reaction is considered complete. The reaction is considered complete when MDTG content is ≤2.0% in area by HPLC.

The reaction mixture is washed with water and with brine until the content of the impurity 2-hydroxy-2,2-bis(2-thienyl) acetic acid (DTG) was ≤1.5%.

The organic solution is concentrated under vacuum at a temperature equal to, or lower than, 50° C. until a final volume of 50 ml.

The suspension was cooled to 20°/25° C. and stirred at this temperature over, at least, 2 hours.

The suspension was cooled to a temperature between 10° C. and 15° C. and stirred at this temperature over, at least, 4 hours.

The product was filtered and washed with isopropyl ether previously cooled to a temperature between 10° C. and 15° C.

The desired product (18.4 g) was obtained with a purity of, not less than 99.20% in area, by HPLC.

Example 2—Transesterification Reaction

Synthesis of (3R)-azabicyclo[2.2.2]oct-3-yl hydroxy (di-2-thienyl)acetate (Compound IV)

A solution of (3R)-quinuclidinol (5.15 g, 40.5 mmol) in 250 ml of toluene is heated until a temperature between 65° C. and 70° C. and sodium methoxide (0.65 g, 11.8 mmol) was added.

Under a flow of nitrogen at a temperature between 75° C. and 85° C. a solution of MDTG (10.0 g; 39.3 mmol) in 100 ml of toluene was added during around 1 hour.

Under a flow of nitrogen and at a temperature between 75° C. and 85° C. the azeotrope of toluene and methanol was removed by distillation (with replacement of fresh toluene) until the reaction is considered complete.

The reaction mixture is washed with a 20% aqueous solution of NaCl four times, until the content of DTG by-product in organic phase was ≤1.5%.

The organic phase was dried and concentrated under vacuum at a temperature equal to, or lower than 40° C. until a final volume of 25 ml.

The suspension was cooled to 10°/15° C. and stirred at this temperature, at least, 5 hours.

The desired product (8.5 g) was obtained with a purity of, not less than 98.0% by HPLC Example 3—Quaternization Reaction Synthesis of aclidinium bromide—(3R)-3-[2-Hydroxy(di-2-thienyl)acetoxy]-1-(3-phenoxypropyl)-1-azoniabicyclo[2.2.2]octane bromide (Compound I)

In an inert atmosphere, to a suspension of (3R)-Azabicyclo[2.2.2]oct-3-yl hydroxy(di-2-thienyl)acetate (5 g; 14.26 mmol) in 30 ml of DMF, 3-phenoxypropyl bromide (3.42 ml, 21.68 mmol) was added slowly at a temperature between 20° C. and 25° C.

The suspension was stirred at about 30° C. until the content of the starting material content is below 0.5% in area by HPLC.

When the reaction was completed acetonitrile (43 ml) was added to the suspension. The suspension was cooled at a temperature between 20° C. and 25° C. and stirred over 2 hours while maintaining the temperature between 20° C. and 25° C.

The product was filtered and washed with acetonitrile, previously cooled to a temperature between 10° C. and 15° C.

Aclidinium bromide was obtained (7.48 g) with a purity of 99.4% in area by HPLC.

Examples 4 to 8—Quaternization Reaction

In examples 4 to 8, the process followed was the process described in example 3 where different quantities of the reaction solvent and of the reagent 3-phenoxypropyl bromide were used.

| Ex: | Equivalents of 3-phenoxypropyl bromide | Solvent | Amount of solvent ml/g | Reaction temperature (° C.) | Reaction time (h) | Yield (%) |
|---|---|---|---|---|---|---|
| 4 | 1.88 | DMF | 8.6 | 30 |  | 91 |
| 5 | 1.88 | DMF | 3.7 | 30 | 3.5 | 90.8 |
| 6 | 1.16 | DMF | 3.7 | 30 | 6.5 | 90.6 |
| 7 | 1.52 | DMF | 6.15 | 30 |  | 88.8 |
| 8 | 1.52 | DMF | 6.15 | 20 | 7 | 92.2 |

Using DMF as solvent the selected parameters were: 1.88 eq of 3-phenoxypropyl bromide; amount of solvent 3.7 ml/g; temperature 30° C.

Example 9—Quaternization Reaction

Synthesis of aclidinium bromide—(3R)-3-[2-Hydroxy(di-2-thienyl)acetoxy]-1-(3-phenoxypropyl)-1-azoniabicyclo[2.2.2]octane bromide (Compound I)

In an inert atmosphere, to a suspension of (3R)-Azabicyclo[2.2.2]oct-3-yl hydroxy(di-2-thienyl)acetate (5 g, 14.26 mmol) in 30 ml of DMA, 3-phenoxypropyl bromide (4.23 ml, 26.82 mmol) was added slowly at a temperature between 20° C. and 25° C.

The suspension was stirred at 30° C. until the content of the starting material content is below 0.5% in area by HPLC.

When the reaction was completed, acetonitrile (43 ml) was added to the suspension. The suspension was cooled at a temperature between 20° C. and 25° C. and stirred over 2 hours while maintaining the temperature between 20° C. and 25° C.

The product was filtered and washed with acetonitrile, previously cooled to a temperature between 10° C. and 15° C.

Aclidinium bromide is obtained (7.4 g) with a purity of 98.98% in area by HPLC.

Example 10—Quaternization Reaction

Synthesis of aclidinium bromide—(3R)-3-[2-Hydroxy(di-2-thienyl)acetoxy]-1-(3-phenoxypropyl)-1-azoniabicyclo[2.2.2]octane bromide (Compound I)

In an inert atmosphere, to a suspension of (3R)-azabicyclo[2.2.2]oct-3-yl hydroxy(di-2-thienyl)acetate (4.50 g, 12.84 mmol) in 27.7 ml of DMSO, 3-phenoxypropyl bromide (3.80 ml, 24.14 mmol) was added at a temperature of about 30° C.

The suspension was stirred at 30° C. until the content of the starting material content is below 0.5% in area by HPLC.

When the reaction is completed, acetonitrile (54 ml) was added to the suspension; the suspension was cooled at a temperature between 20° C. and 25° C. and stirred over 2 hours while maintaining the temperature between 20° C. and 25° C.

The product was filtered and washed with acetonitrile previously cooled to a temperature between 10° C. and 15° C.

Aclidinium bromide was obtained (5.8 g) with a purity of 99.88% in area by HPLC.

Example 11—Purification of Compound (I)

Purification of aclidinium bromide—(3R)-3-[2-hydroxyl(di-2-thienyl)acetoxy]-1-(3-phenoxypropyl)-1-azoniabicyclo[2.2.2]octane bromide (Compound I)

In an inert atmosphere, (3R)-3-[2-Hydroxy(di-2-thienyl)acetoxy]-1-(3-phenoxypropyl)-1-azoniabicyclo[2.2.2]octane bromide (50 g) was added to 500 ml of dimethylsulfoxide at a temperature between 40° C. and 45° C. To the solution obtained, 1 l of acetonitrile was added slowly.

The product crystallized and a slowly cooling was done until a temperature between 20° C. and 25° C.

The suspension was stirred over 2 hours while maintaining the temperature between 20° C. and 25° C.

Aclidinium bromide purified was obtained (33 g) and with a purity of 99.91% in area by HPLC.

Example 12—Micronization

Micronization was conducted by jet milling in order to conclude if the particle size distribution (PSD) of the aclidinium bromide could be easily adjusted to a range suitable for inhalation (1-5 μm). A 1.5" jet miller (Fluid Jet Mill J20/DS20) was used for the micronization fed with pure nitrogen. In this example the powder was added at constant flow rate by a double-screw type feeder, with Venturi and nozzles pressure between 4 to 10 bar.

Figure 8:
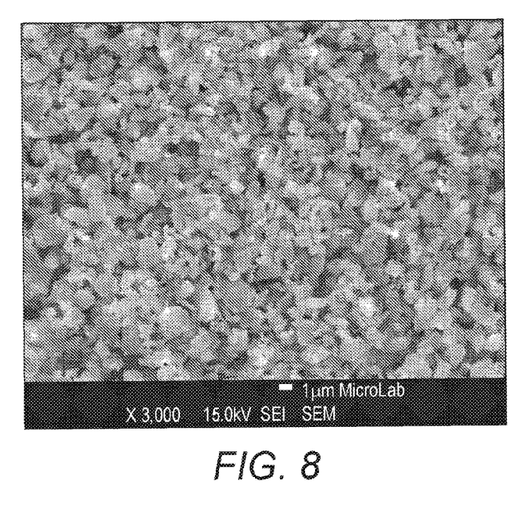
FIG. 8—depicts the Scanning Electron Microscopy (SEM) of the product after micronization.

The analytical results obtained are summarized in the table below. The product obtained had a PSD within the inhalable range with a purity higher than 99.5% and high yield (90% wt.). With only one passage the powder reached the desirable PSD, and no presence of amorphous material could be detected on the product. In addition the SEM image of the micronized material revealed a homogeneous PSD (FIG. 8).

| Batch | Dv10; Dv50; Dv90 | HPLC purity (area) |
|---|---|---|
| Starting raw material | 6.1; 15.5; 35.9 | 99.9% |
| Product after 1 cycle Batch 1 | 1.3; 2.4; 4.6 | 99.7% |
| Product after 1 cycle Batch 2 | 1.5; 2.6; 4.8 | 99.5% |

Measuring Conditions

All XRPD were obtained using high throughput XRPD set-up. Data collection was carried out at room temperature using monochromatic $CuK_\alpha$, radiation in the 2θ region between 1.5° and 41.5°.

TGA/DSC

The instrument used was TGA/SDRA 851e (Mettler-Toledo) that was calibrated for temperature with In and Al. The seals were pin holed and the crucible heated in the TGA from 25° C. to 300° C., at a heating rate of 10° C./min

SEM

The instrument used was a Phillips SEM 525 microscope equipped with an external SE detector.

The invention claimed is:

1. A process for preparing (3R)-3-[2-Hydroxy(di-2-thienyl)acetoxy]-1-(3-phenoxypropyl)-1-azoniabicyclo[2.2.2] octane bromide (aclidinium bromide) by reacting 2-hydroxy-2,2-dithien-2-ylacetic acid 1-azabicyclo[2.2.2]oct-3 (R) yl methyl ester and 3-phenoxypropyl bromide, wherein the reaction takes place in a solvent or mixture of solvents selected from the group of amides and/or the group of solvents with a sulfoxide group.

2. The process according to claim 1 wherein the reaction temperature is below 100° C.

3. The process according to claim 1 wherein the reaction temperature is from about 30° C. to about 20° C.

4. The process according to claim 1 wherein the reaction temperature is about 20° C.

5. The process according to claim 1 wherein the reaction takes place under a flow of an insert gas.

6. The process according to claim 1 wherein the reaction takes place at a pressure below the atmospheric pressure.

7. The process according to claim 1 wherein the alcohol formed is removed from the reaction mixture.

8. The process according to claim 1 wherein the solvent is DMF or is a mixture of solvents containing DMF.

9. The process according to claim 1 wherein the solvent is DMA or is a mixture of solvents containing DMA.

10. The process according to claim 1 wherein the solvent is DMSO or is a mixture of solvents containing DMSO.

11. The process according to claim 1 wherein the equivalent mole ratio of 3-phenoxypropyl bromide to 2-hydroxy-2,2-dithien-2-ylacetic acid 1-azabicyclo[2.2.2]oct-3(R) yl methyl ester is in the range of from 1.2 to 2.0.

12. The process according claim 11 wherein the range is from 1.5 to 2.0.

13. The process according to claim 1 wherein the reaction time is not more than 8 hours.

14. The process according to claim 13 wherein the reaction time is not more than 6 hours.

15. The process according to claim 1 further comprising the step of purification of aclinidium bromide by dissolving the product in DMSO and using acetonitrile as co-solvent to precipitate the purified product.

16. The process according to claim 1 wherein the aclidinium bromide obtained is crystalline.

17. The process according to claim 16 wherein the aclidinium bromide is characterized by a powder XRPD pattern having peaks at 7.7±0.2° 2θ, 10.4±0.2° 2θ, 13.2±0.2° 2θ, 13.8±0.2° 2θ, 19.9±0.2° 2θ, 20.3±0.2° 2θ, 20.8±0.2° 2θ, 24.2±0.2° 2θ, 25.7±0.2° 2θ, 26.1±0.2° 2θ, 29.2±0.2° 2θ, 30.8±0.2° 2θ.

18. The process according to claim 17, wherein the aclidinium bromide is further characterized by no weight loss by TGA.

19. The process according to claim 17, wherein the aclidinium bromide is further characterized by a DSC thermogram having an endotherm peak at 228° C.

20. The process according to claim 1 where the aclidinium bromide obtained is a mixture of crystalline and amorphous material.

21. The process according to claim 20 where the mixture of crystalline and amorphous aclidinium bromide is characterized by a powder XRPD pattern as depicted in FIG. 9.

22. The process according to claim 20 wherein 20 wt % or less, as a percentage of the total weight of material, of amorphous aclidinium bromide is present.

23. The process according to claim 1 further comprising drying a solution comprising aclidinium bromide in a solvent or a mixture of solvents.

24. The process according to claim 23 wherein the said solvent or mixture of solvents are selected from the group of solvents with a sulfoxide group.

25. The process according to claim 23 wherein the said mixture of solvents contain at least one solvent selected from the group of solvents with a sulfoxide group.

26. The process according to claim 23 wherein the said mixture of solvents contain DMSO.

27. The process according to claim 23 wherein the said solvent is DMSO.

28. The process according to claim 1 wherein the reaction temperature is below 50° C.

29. The process according to claim 1 wherein the reaction temperature is about 30° C.

30. The process according to claim 1 wherein the reaction takes place under a flow of a dry inert gas.

31. The process according to claim 1 wherein the reaction takes place under a flow of dry nitrogen, dry helium or a mixture thereof.

32. The process according claim 11 wherein the equivalent mole ratio of 3-phenoxypropyl bromide to 2-hydroxy-2,2-dithien-2-ylacetic acid 1-azabicyclo[2.2.2]oct-3(R) yl methyl ester is 1.8.

33. The process according to claim 13 wherein the reaction time is not more than 4 hours.

34. The process according to claim 20 wherein 10 wt % or less, as a percentage of the total weight of material, of amorphous aclidinium bromide is present.

35. The process according to claim 1 further comprising drying a solution of aclidinium bromide in a solvent or a mixture of solvents by spray drying.

* * * * *

UNITED STATES PATENT AND TRADEMARK OFFICE
CERTIFICATE OF CORRECTION

PATENT NO. : 10,087,177 B2
APPLICATION NO. : 15/562814
DATED : October 2, 2018
INVENTOR(S) : Zita Mendes et al.

It is certified that error appears in the above-identified patent and that said Letters Patent is hereby corrected as shown below:

In the Claims

Claim 5, Column 10, Line 23, replace "insert" with --inert--

Signed and Sealed this
Fourth Day of December, 2018

Andrei Iancu
*Director of the United States Patent and Trademark Office*